United States Patent [19]
Yoshioka et al.

[11] Patent Number: 5,705,638
[45] Date of Patent: Jan. 6, 1998

[54] PROCESS FOR PREPARING OPTICALLY ACTIVE 3-HYDROXY-1,5-BENZOTHIAZEPINE DERIVATIVE AND INTERMEDIATE THEREFOR

[75] Inventors: Ryuzo Yoshioka, Mishima-gun; Shin-ichi Yamada, Takarazuka; Takeji Shibatani, Kobe, all of Japan

[73] Assignee: Tanabe Seiyaku Co., Ltd., Osaka, Japan

[21] Appl. No.: 744,817

[22] Filed: Nov. 6, 1996

[30] Foreign Application Priority Data

Dec. 5, 1995 [JP] Japan ................... 7-316153

[51] Int. Cl.$^6$ ................................. C07D 281/10
[52] U.S. Cl. ................................. 540/491
[58] Field of Search .................. 540/491; 514/211

[56] References Cited

U.S. PATENT DOCUMENTS

| | | | |
|---|---|---|---|
| 3,562,257 | 2/1971 | Kugita et al. | 540/491 |
| 4,567,175 | 1/1986 | Takeda et al. | 514/211 |
| 5,134,139 | 7/1992 | Kawai et al. | 514/211 |

FOREIGN PATENT DOCUMENTS

| | | |
|---|---|---|
| 0488210 | 6/1992 | European Pat. Off. |
| 46-43785 | 12/1971 | Japan. |
| 53-18038 | 6/1978 | Japan. |
| 59-20273 | 2/1984 | Japan. |

OTHER PUBLICATIONS

J. Jacques, et al., *Enantiomers, Racemates, and Resolutions*, Krieger Publishing Co., Malabar, Florida, 1991, pp. 256, 259, and 260.

"Separation of the Optical Isomer," *Chemical Society of Japan*, No. 6 (1989), pp. 5-8.

H. Nohira, "Optically Active Compounds—Industrial Organic Chemistry Thereof," 1989, pp. 67-77.

N.L. Allinger, et al., *Topics in Stereochemistry*, vol. 6, (1972) Wiley-Interscience, New York, p. 108.

Y. Zasshi, "Synthesis of 1,5-Benzothiazepine Derivatives. IV. Resolution of dl-cis-3-Acetoxy-5-[2-(dimethylamino) ethyl]-2,3-dihydro-2-(p-methoxyphenyl)-1,5-benzothiazepin-4(5H)-one Hydrochloride," *UDC*, vol. 93, No. 6 (1973), pp. 729-732.

H. Kugita et al., "Synthesis of 1,5-Benzothiazepine Derivatives. III," *Chemical and Pharmaceutical Bulletin*, vol. 19, No. 3 (1971), pp. 595-602.

*Primary Examiner*—Richard L. Raymond
*Attorney, Agent, or Firm*—Finnegan, Henderson, Farabow, Garrett & Dunner, L.L.P.

[57] ABSTRACT

An optical resolution process of the compound of the formula (1):

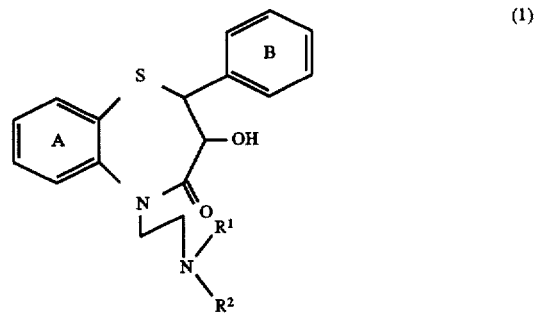

wherein Ring A and Ring B are a substituted or unsubstituted benzene ring and $R^1$ and $R^2$ are the same or different and a lower alkyl group, by utilizing difference in solubility between the two diastereoisomeric salts prepared by treating the racemic compound (1) with an acidic resolution agent. The present process is industrially advantageous with compared to conventional processes for preparing an optically active 3-hydroxy-1,5-benzothiazepine derivative which are useful as an intermediate for preparing medicines.

11 Claims, No Drawings

PROCESS FOR PREPARING OPTICALLY ACTIVE 3-HYDROXY-1,5-BENZOTHIAZEPINE DERIVATIVE AND INTERMEDIATE THEREFOR

This invention relates to a novel process for preparing an optically active 3-hydroxy-1,5-benzothiazepine derivative and novel optically active acid addition salt of 3-hydroxy-1,5-benzothiazepine derivative. In more particular, it relates to a novel process for optically resolving a racemic cis-3-hydroxy-1,5-benzothiazepine derivative or an acid addition salt thereof by using an optically active 3-bromocamphor-9-sulfonic acid or a salt thereof as a resolving agent and a novel 3-bromocamphor-9-sulfonic acid addition salt of 3-hydroxy-1,5-benzothiazepine derivative.

PRIOR ART

The optically active cis-3-hydroxy-1,5-benzothiazepine derivative or an acid addition salt thereof obtained by the process of the present invention is a very important compound, for example, as a key intermediate for the synthesis of Diltiazem Hydrochloride(Chemical name: (2S, 3S)-cis-3-acetoxy-2,3-dihydro-5-[2-(dimethylamino)ethyl]-2-(4-methoxyphenyl)-1,5-benzothiazepin-4(5H)-one hydrochloride), which is widely used as a calcium-channel blocker for a treatment of angina pectoris, essential hypertension and the like.

Among the known various processes for optical resolution of organic compounds, a process utilizing different solubility of two diastereoisomeric salts produced by treating a racemic compound with an optically active resolving agent (Diastereoisomeric salts method) is one of the industrially advantageous process.

However, it is difficult to predict that what kind of resolving agent is suitable for the efficient optical resolution of an objective racemic compound, and so it is a common general knowledge in the technical field that researches on the optical resolution using a resolving agent must be carried out through trial and error approach [Chemical Society of Japan: "Separation of the Optical Isomer", Kagakusosetsu (the Introduction of Chemistry), No.6, pp.5–8, (1989); H. Nohira: "Optically Active Compounds-Industrial Organic Chemistry thereof", p.75, (1989); Allinger, N. L., E. L. Eliel:"Topics in Stereochemistry", vol.6, p.108, John Wiley & Sons, Wiley-Interscience New York, (1971)].

In other words, even if one racemic compound can be resolved efficiently by using one resolving agent, it is generally difficult to predict not only whether the other racemic compounds similar in chemical structure to said racemic compound can be optically resolved efficiently by using the same or similar resolving agent as mentioned above but also whether a resultant diastereoisomeric salt can be crystallized or not.

Japanese Patent First Publication (Kokai) No. 20273/1984 discloses that 3-acetoxy-1,5-benzothiazepine derivative of the formula (4):

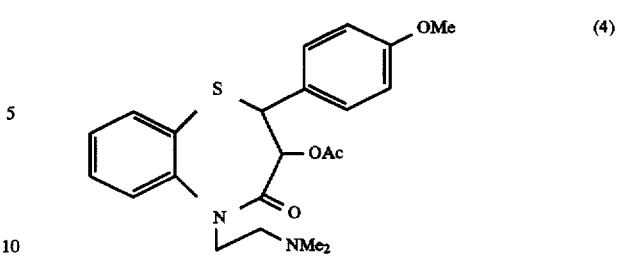

can be optically resolved by using an optically active camphor-10-sulfonic acid or an optically active malic acid.

On the other hand, it has been reported in Yakugaku Zasshi, 93(6), p.729 (1973) that it is extremely difficult to carry out the optical resolution of 3-hydroxy-1,5-benzothiazepine derivative of the formula (1-a):

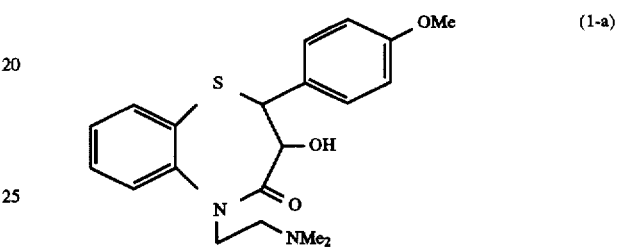

and in case of the optical resolution by using an optically active camphor-10-sulfonic acid as a resolving agent, a small amount of (+)-3-hydroxy-1,5-benzothiazepine derivative of the formula (1-a) is barely obtained by 15 times repeated recrystallization.

As mentioned above, while the efficient optical resolution process of a racemic 3-acetoxy-1,5-benzothiazepine derivative (4) has been found, the useful and efficient optical resolution process of the racemic 3-hydroxy-1,5-benzothiazepine derivative has not been found yet. Hence, it has been desired to develop convenient and practical process for the optical resolution of 3-hydroxy-1,5-benzothiazepine derivative in an industrial scale.

Under the above mentioned circumstances, as a result of various investigations in order to establish a novel process for the optical resolution of 3-hydroxy-1,5-benzothiazepine derivative, the present inventors could find that a highly purified optically active 3-hydroxy-1,5-benzothiazepine derivative can be easily obtained in high yield by a simple process including a step of treating a racemic cis-3-hydroxy-1,5-benzothiazepine derivative or an acid addition salt thereof with an optically active 3-bromocamphor-9-sulfonic acid or a salt thereof in a solvent to form novel diastereoisomeric salts, and could accomplish the present invention. To put it more concretely, an optically active 3-hydroxy-1, 5-benzothiazepine derivative can be obtained by treating (±)-cis-(2RS,3RS)-5-[2-(di-lower alkylamino)ethyl]-2,3-dihydro-3-hydroxy-2-(substituted or unsubstituted phenyl)-1,5-substituted or unsubstituted benzothiazepin-4(5H)-one with an optically active 3-bromocamphor-9-sulfonic acid in an appropriate solvent to form two novel diastereoisomeric salts, followed by crystallizing and separating a less-soluble diastereoisomeric salt from the other by utilizing difference in solubility between the two diastereoisomeric salts. According to the present invention, a highly purified optically active 3-hydroxy-1,5-benzothiazepine derivative can be easily obtained in high yield even without recrystallization.

3
BRIEF DESCRIPTION OF THE INVENTION

An object of the present invention is to provide a novel process for preparing an optically active 3-hydroxy-1,5-benzothiazepine derivative, which is a useful synthetic intermediate for preparing medicine like Diltiazem Hydrochloride.

Another object of the present invention is to provide a novel 3-bromocamphor- 9-sulfonic acid addition salt of 3-hydroxy-1,5-benzothiazepine derivative which is an intermediate for preparing an optically active 3-hydroxy-1,5-benzothiazepine derivative.

Still further object of the present invention is to provide a process for preparing an optically active 3-lower alkanoyloxy-1,5-benzothiazepine derivative by using said optically active 3-hydroxy-1,5-benzothiazepine derivative.

DETAILED DESCRIPTION OF THE INVENTION

According to the present invention, an optically active cis-3-hydroxy-1,5-benzothiazepine derivative (1) or an acid addition salt thereof can be prepared by treating a racemic cis-3-hydroxy-1,5-benzothiazepine derivative of the formula (1):

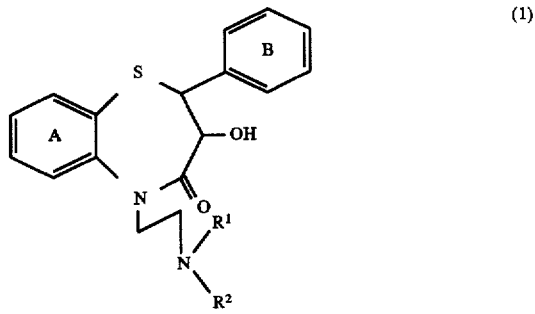

wherein Ring A and Ring B are substituted or unsubstituted benzene rings and $R^1$ and $R^2$ are the same or different lower alkyl groups, or an acid addition salt thereof with an optically active d- or l-3-bromocamphor-9-sulfonic acid or a salt thereof to form two diastereoisomeric salts of the formula (2):

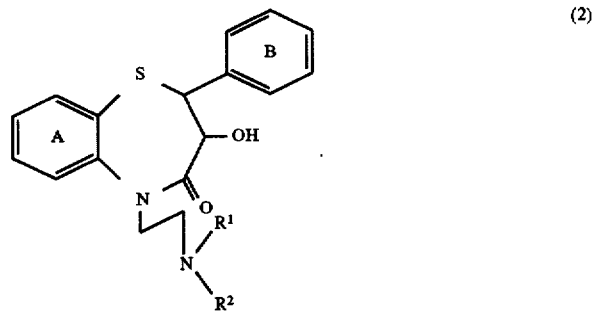

4

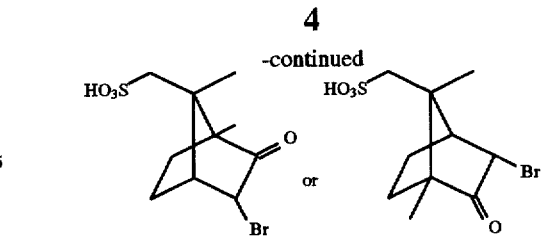

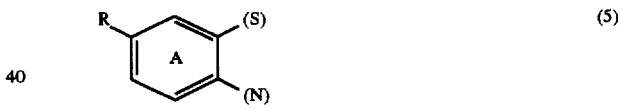

wherein the symbols are the same as defined above, separating and collecting one diastereoisomeric salt from the mixture of two diastereoisomeric salts by utilizing difference in solubility between the two diastereoisomeric salts, converting the collected salt into a free base or an acid addition salt thereof other than the diastereoisomeric salt of the formula (2).

In the present invention, Ring A and Ring B of 3-hydroxy-1,5-benzothiazepine derivative of the formula (1) and (2) may be the same or different and unsubstituted benzene rings or benzene rings having a substituent selected from a lower alkyl group, a lower alkoxy group and a halogen atom at any position of the benzene ring. $R^1$ and $R^2$ are the same or different lower alkyl groups.

Examples of the lower alkyl group include a straight-chain or branched-chain alkyl group having 1 to 6 carbon atoms such as a methyl group, an ethyl group, a propyl group, an isopropyl group, a butyl group or an isobutyl group. Examples of the lower alkoxy group include a straight-chain or branched-chain alkoxy group having 1 to 6 carbon atoms such as a methoxy group, an ethoxy group, a propoxy group, an isopropoxy group or a butoxy group. Examples of the halogen atom include chlorine, bromine, fluorine or iodine.

Among them, preferred example of Ring A includes a benzene ring of the formula (5):

$$\text{(5)}$$

wherein R is a hydrogen atom, a methyl group, a methoxy group or chlorine, and preferred example of Ring B includes a benzene ring substituted by a methoxy group or a methyl group at 4-position thereof. Besides, preferred examples of $R^1$ and $R^2$ include methyl groups.

Further preferred example of Ring A is an unsubstituted benzene ring and further preferred example of Ring B is a benzene ring substituted by a methoxy group at 4-position thereof. Further preferred examples of $R^1$ and $R^2$ are methyl groups.

The process of the present invention is carried out by treating a racemic cis- 3-hydroxy-1,5-benzothiazepine derivative (1) with an optically active 3-bromocamphor-9-sulfonic acid in an appropriate solvent, if necessary, heating the mixture to dissolve the resultant diastereoisomeric salts, cooling the mixture to form crystals of a less-soluble diastereoisomeric salt (2) optionally with stirring, collecting the precipitated crystals and converting the salt into a free base or an acid addition salt thereof.

According to the present invention, the desired optically active compound (1) can be obtained from a racemic cis-3-hydroxy-1,5-benzothiazepine derivative (1). That is, when d-3-bromocamphor-9-sulfonic acid is used as a resolving agent, there can be obtained a (2S,3S)-cis-3-hydroxy-1,5- benzothiazepine derivative (1), and when 1-bromocamphor-9-sulfonic acid is used as a resolving agent, there can be obtained a (2R,3R)-cis-3-hydroxy-1,5-benzothiazepine derivative (1), respectively.

The racemic cis-3-hydroxy-1,5-benzothiazepine derivative (1) to be used as a starting material in the present invention may be not only a 1:1 mixture of (2S,3S)-isomer and (2R,3R)-isomer (i.e., real racemate), but also a mixture of any ratio of both isomers. The racemic cis-3-hydroxy-1,5-benzothiazepine derivative (1) may be used either in the form of free base or in the form of an acid addition salt thereof (e.g., a salt with mineral acid such as hydrochloride, sulfate or phosphate or a salt with organic acid such as oxalate or benzenesulfonate).

The optically active 3-bromocamphor-9-sulfonic acid used as a resolving agent in the present invention may be used either in the form of free acid or in the form of a salt thereof (e.g., alkaline earth metal salt such as sodium salt or potassium salt, ammonium salt, or an organic base salt such as methylamine salt or benzylamine salt).

The amount of the optically active 3-bromocamphor-9-sulfonic acid as a resolving agent used in the present invention is not particularly limited, however, it is preferred to use said resolving agent in an amount of 0.5 to 1.5 mole to 1 mole of a racemic cis-3-hydroxy-1,5-benzothiazepine derivative (1).

Preferred examples of the solvent used in the present invention include water; alcohols such as methanol, ethanol or propanol; ketones such as acetone or methyl ethyl ketone; esters such as ethyl acetate; aromatic hydrocarbons such as benzene, toluene or xylene; halogenated hydrocarbons such as chloroform; or saturated aliphatic hydrocarbons such as hexane or cyclohexane.

The solvents mentioned above can be used either independently or, if necessary, as a mixture of two or more solvents in an appropriate proportion. In particular, the mixture of water and alcohols is preferable.

The precipitation of a less-soluble diastereoisomeric salt from the mixture can be carried out at a temperature from a solidifying temperature to a boiling temperature of the solvent used therein, and preferably at a temperature from a room temperature to a boiling temperature of the solvent used therein.

In the present invention, the less-soluble diastereoisomeric salt is readily precipitated and it is not necessary to seed crystals into the mixture, but the crystals of the desired diastereoisomeric salt may be seeded into the mixture at an appropriate temperature for the effective resolution.

The precipitated crystals of the less-soluble diastereoisomeric salt can be easily separated and collected from the mixture by a conventional solid-liquid separation method such as filtration, centrifugation and the like. The obtained crystals have a sufficiently high optical purity, but if required, the purity thereof can be further improved by recrystallization.

The obtained diastereoisomeric salt (2) may be subjected to any conventional process for converting the diastereoisomeric salt into a free base or an acid addition salt thereof.

For example, the conversion of the diastereoisomeric salt may be carried out by dissolving said salt in water or alcohol and neutralizing the solution with a base such as sodium hydrogen carbonate, sodium hydroxide, triethylamine or pyridine, followed by collecting precipitated crystals. Said conversion may be also carried out by neutralizing the solution of the diastereoisomeric salt with a base and extracting with an organic solvent such as ethylacetate.

The resolving agent, i.e., the optically active 3-bromocamphor-9-sulfonic acid remaining in the mother liquor obtained after the conversion of the salt can be recovered in the form of free acid by treating the mother liquor with a strong acidic ion-exchange resin, or in the form of a crystalline salt thereof by adding a base into the mother liquor. The recovered resolving agent can be used repeatedly.

A (+)-rich or (−)-rich compound (1) remaining in the mother liquor obtained after filtration of the less-soluble diastereoisomeric salt (2) can be recovered by neutralizing the mother liquor with a base described above and collecting the precipitated crystals, or by neutralizing the mother liquor with a base and extracting with ethyl acetate. Besides, from the resulting mother liquor obtained after recovering the compound (1), the resolving agent, i.e., the optically active 3-bromocamphor-9-sulfonic acid used can be recovered in the same manner described above and the recovered resolving agent can be used repeatedly.

The obtained optically active 3-hydroxy-1,5-benzothiazepine derivative (1) or an acid addition salt thereof can be converted into an optically active 1,5-benzothiazepine derivative of the formula (3):

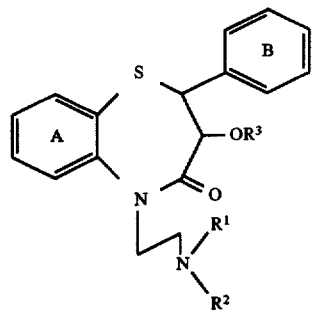

(3)

wherein $R^3$ is a lower alkanoyl group and the other symbols are the same as defined above, in accordance with a conventional method, and if necessary, further converting the product into a pharmaceutically acceptable salt thereof.

That is, an optically active 1,5-benzothiazepine derivative (3) can be prepared by introducing a lower alkanoyl group on the hydroxy group at the 3-position of the optically active 3-hydroxy-1,5-benzothiazepine derivative (1) or an acid addition salt thereof in accordance with a conventional method disclosed in Japanese Patent Second Publication (Kokoku) No. 16988/1971, Japanese Patent Second Publication (Kokoku) No. 43785/1971, Japanese Patent Second Publication (Kokoku) No. 813/1972, Japanese Patent Second Publication (Kokoku) No. 18038/1978, Japanese Patent Second Publication (Kokoku) No. 13994/1988 or Japanese Patent First Publication (Kokai) No. 157378/1991, and if necessary, further converting the product into a pharmaceutically acceptable salt thereof.

For example, 1,5-benzothiazepine derivative (3) can be prepared by condensing a 3-hydroxy-1,5-benzothiazepine derivative (1) with a compound of the formula [6]:

$R^3OH$         (6)

wherein R³ is a lower alkanoyl group, or a reactive derivative thereof.

Throughout the present claims and specification, the lower alkanoyl group means a straight-chain or branched-chain alkanoyl group having 2 to 6 carbon atoms such as acetyl group, propionyl group, isopropionyl group, butanoyl group, pentanoyl group or hexanoyl group, d-3-bromocamphor-9-sulfonic acid means [(1R)-(endo, anti)]-(+)-3-bromo-1,7-dimethyl-7-sulfomethylbicyclo[2.2.1]heptan-2-one and l-3-bromocamphor-9-sulfonic acid means [(1S)-(endo, anti)]-(−)-3-bromo-1,7-dimethyl-7-sulfomethylbicyclo[2.2.1]heptan-2-one.

The starting material, i.e., 3-hydroxy-1,5-benzothiazepine derivative (1) used in the present invention can be easily obtained in accordance with, for example, the method disclosed in Chemical and Pharmaceutical Bulletin (Chem. Pharm. Bull.), 19, 595, 1971.

The present invention is illustrated concretely by the following Examples, but should not be construed to be limited thereto.

EXAMPLES

Example 1

To 2.0 g of (±)-(2RS,3RS)-cis-2,3-dihydro-5-[2-(dimethylamino)ethyl]-3-hydroxy-2-(4-methoxyphenyl)-1,5-benzothiazepin-4(5H)-one are added 7.45 g of aqueous solution (22.9 wt %) of d-3-bromocamphor-9-sulfonic acid, 19.4 ml of water and 8 ml of methanol, and the mixture is heated to dissolve the benzothiazepine compound at 70°–90° C. The mixture is gradually cooled, and then stirred at room temperature for two hours. The precipitated crystals are collected by filtration, washed with a small amount of cold water/methanol (=4/1) and dried under reduced pressure at 50° C. to give 1.72 g of (+)-(2S,3S)-cis-2,3-dihydro-5-[2-(dimethylamino)ethyl]-3-hydroxy-2-(4-methoxyphenyl)-1,5-benzothiazepin-4(5H)-one d-3-bromocamphor-9-sulfonate (Yield: 46.9% (calculated based on the amount of the (±)-(2RS,3RS)-compound used), $[\alpha]_D^{25}$: +107.0° (c=1, MeOH)). 0.68 g of the obtained salt is suspended in 30 ml of water, and thereto is added 0.09 g of sodium hydrogencarbonate. The aqueous mixture is extracted with ethyl acetate three times. The organic layer is washed with a saturated saline solution, dried over anhydrous magnesium sulfate, and evaporated to remove the solvent. 0.35 g of Crystalline (+)-(2S,3S)-cis-2,3-dihydro-5-[2-(dimethylamino)ethyl]-3-hydroxy-2-(4-methoxyphenyl)-1,5-benzothiazepin-4(5H)-one is thereby obtained.

M.P.: 86°–88° C. $[\alpha]_D^{25}$: +168.8° (c=1, MeOH) Optical purity: 98.8%

Example 2

To 2.0 g of (±)-(2RS,3RS)-cis-2,3-dihydro-5-[2-(dimethylamino)ethyl]-3-hydroxy-2-(4-methoxyphenyl)-1,5-benzothiazepin-4(5H)-one are added 1.79 g of d-3-bromocamphor-9-sulfonic acid ammonium salt, 25 ml of water, 8 ml of methanol and 0.91 ml of 6N-HCl, and the mixture is heated to dissolve the above mentioned compounds at 70°–90° C. The mixture is gradually cooled, and then stirred at room temperature for two hours. The precipitated crystals are collected by filtration, washed with a small amount of cold water/methanol (=4/1) and dried under reduced pressure at 50° C. to give 1.60 g of (+)-(2S,3S)-cis-2,3-dihydro-5-[2-(dimethylamino)ethyl]-3-hydroxy-2-(4-methoxyphenyl)-1,5-benzothiazepin-4(5H)-one d-3-bromocamphor-9-sulfonate (Yield: 43.6% (calculated based on the amount of the (±)-(2RS,3RS)-compound used), $[\alpha]_D^{25}$: +108.4° (c=1, MeOH)). 1.5 g of the obtained salt are recrystallized from a mixture of 15 ml of water and 0.5 ml of ethanol to give 1.42 g of crystalline (+)-(2S,3S)-cis-2,3-dihydro-5-[2-(dimethylamino)ethyl]-3-hydroxy-2-(4-methoxyphenyl)-1,5-benzothiazepin-4(5H)-one d-3-bromocamphor-9-sulfonate (Yield: 94.7%, $[\alpha]_D^{25}$: +112.2° (c=1 MeOH)). 1.37 g of the recrystallized salt are converted in the same manner as described in Example 1 into 0.70 g of (+)-(2S,3S)-cis-2,3-dihydro-5-[2-(dimethylamino)ethyl]-3-hydroxy-2-(4-methoxyphenyl)-1,5-benzothiazepin-4(5H)-one.

M.P.: 86°–88° C. $[\alpha]_D^{25}$: +170.8° (c=1 MeOH) Optical purity: 100%

Example 3

To 4.0 g of (±)-(2RS,3RS)-cis-2,3-dihydro-5-[2-(dimethylamino)ethyl]-3-hydroxy-2-(4-methoxyphenyl)-1,5-benzothiazepin-4(5H)-one are added 8.77 g of aqueous solution (22.9 wt %) of d-3-bromocamphor-9-sulfonic acid, 23.2 ml of water, 0.72 ml of 6N-HCl and 9.5 ml of methanol, and the mixture is heated to dissolve the above mentioned compounds at 70°–90° C. The mixture is gradually cooled, and then stirred at room temperature for two hours. The precipitated crystals are collected by filtration, washed with a small amount of cold water/methanol (=4/1) and dried under reduced pressure to give 3.26 g of crystalline (+)-(2S,3S)-cis-2,3-dihydro-5-[2-(dimethylamino)ethyl]-3-hydroxy-2-(4-methoxyphenyl)-1,5-benzothiazepin-4(5H)-one d-3-bromocamphor-9-sulfonate (Yield: 44.4% (calculated based on the amount of the (±)-(2RS,3RS)-compound used), $[\alpha]_D^{25}$: +113.2° (c=1, MeOH))*. 2.73 g of the obtained salt are suspended in 60 ml of water, and thereto is added 0.37 g of sodium hydrogencarbonate. The mixture is extracted with ethyl acetate three times. The organic layer is washed with a saturated saline solution, dried over anhydrous magnesium sulfate, and evaporated to remove the solvent. 1.40 g of crystalline (+)-(2S,3S)-cis-2,3-dihydro-5-[2-(dimethylamino)ethyl]-3-hydroxy-2-(4-methoxyphenyl)-1,5-benzothiazepin-4(5H)-one are thereby obtained.

*The mother liquor after filtration of the salt is evaporated to remove methanol, and thereto is added 0.8 g of sodium hydrogencarbonate. The mixture is extracted with ethyl acetate three times. The organic layer is washed with a saturated saline solution, dried over anhydrous magnesium sulfate, and evaporated to remove the solvent. 2.21 g of crystalline (2R,3R)-cis-2,3-dihydro-5-[2-(dimethylamino)ethyl]-3-hydroxy-2-(4-methoxyphenyl)-1,5-benzothiazepin-4(5H)-one are thereby obtained. $[\alpha]_D^{25}$: −127.8° (c=1, MeOH) Optical purity: 74.8%

M.P.: 86°–88° C. $[\alpha]_D^{25}$: +166.7° (c=1, MeOH) Optical purity: 97.6%

Effect of the Invention

According to the process of the present invention, the optical resolution of a racemic cis-3-hydroxy-1,5-benzothiazepine derivative (1) can be carried out with good selectivity and reproducibility by forming a novel diastereoisomeric salt (2). Besides, the optically active cis-3- hydroxy-1,5-benzothiazepine derivative (1) can be obtained in high yield without complicated steps. Moreover, according to the process of the present invention with extremely high selectivity, a substantially optically pure cis-3-hydroxy-1,5-benzothiazepine derivative (1) can be obtained easily without recrystallization.

What is claimed is:

1. A process for preparing an optically active cis-3-hydroxy-1,5-benzothiazepine compound (1) or an acid addition salt thereof, which comprises treating a racemic cis-3-hydroxy-1,5-benzothiazepine compound represented by the formula (1):

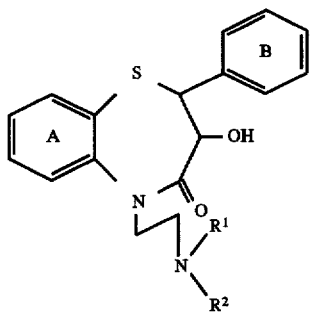

(1)

wherein Ring A and Ring B are substituted or unsubstituted benzene rings and $R^1$ and $R^2$ are the same or different lower alkyl groups, or an acid addition salt thereof with an optically active d- or 1-3-bromocamphor-9-sulfonic acid or a salt thereof in a solvent to form two diastereoisomeric salts of the formula (2):

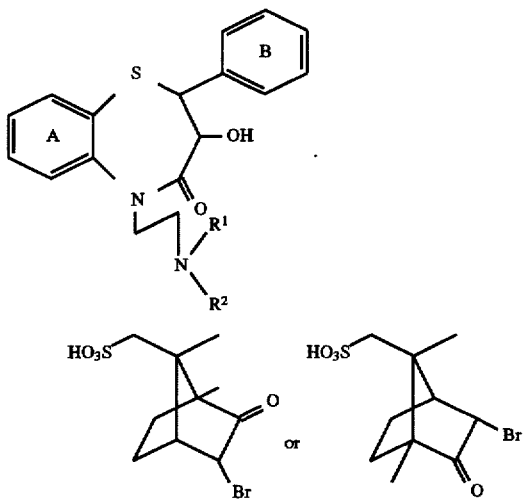

(2)

wherein the symbols are the same as defined above, separating and collecting a less-soluble optically active diastereoisomeric salt by utilizing difference in solubility between the resultant two diastereoisomeric salts, and converting the separated salt into a free base or an acid addition salt other than the diastereoisomeric salt of the formula (2).

2. The process according to claim 1, wherein Ring A is an unsubstituted benzene ring, Ring B is a benzene ring substituted by a methoxy group at the 4-position thereof and $R^1$ and $R^2$ are both methyl groups.

3. The process according to claim 1, wherein the optically active compound (1) to be separated is (2S,3S)-cis-isomer.

4. The process according to claim 2, wherein the optically active compound (1) to be separated is (2S,3S)-cis-isomer.

5. An acid addition salt of 3-hydroxy-1,5-benzothiazepine compound of the formula (2):

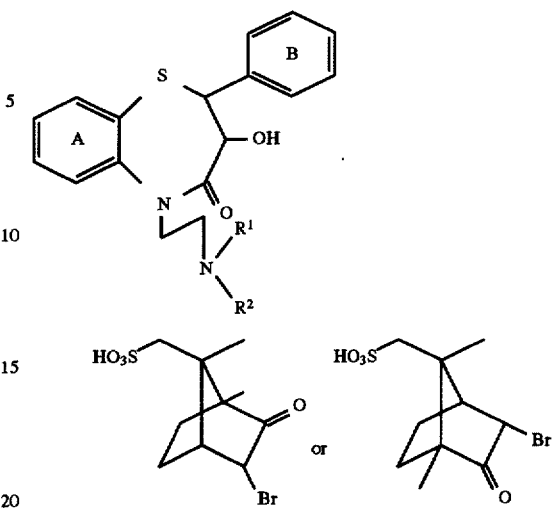

(2)

wherein Ring A and Ring B are substituted or unsubstituted benzene rings and $R^1$ and $R^2$ are the same or different lower alkyl groups.

6. The acid addition salt according to claim 5, wherein Ring A is an unsubstituted benzene ring, Ring B is a benzene ring substituted by a methoxy group at the 4-position thereof and $R^1$ and $R^2$ are both methyl groups.

7. The acid addition salt according to claim 5, wherein the absolute configuration of 2- and 3-positions in 1,5-benzothiazepine moiety is (2S,3S).

8. The acid addition salt according to claim 6, wherein the absolute configuration of 2- and 3-positions in 1,5-benzothiazepine moiety is (2S,3S).

9. A process for preparing an optically active 1,5-benzothiazepine compound (3) or a pharmaceutically acceptable salt thereof, which comprises converting an optically active cis-3-hydroxy-1,5-benzothiazepine compound (1) or an acid addition salt obtained by the process of claim 1 into an optically active 1,5-benzothiazepine compound of the formula (3):

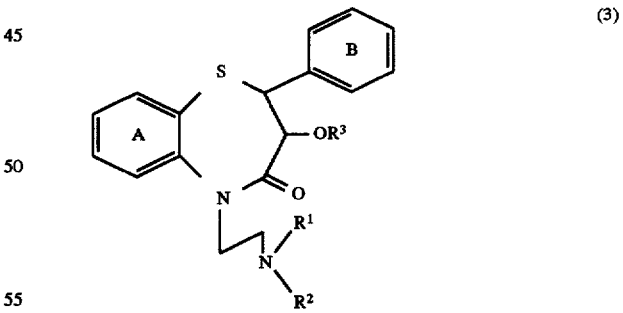

(3)

wherein $R^3$ is a lower alkanoyl group and the other symbols are the same as defined above, by a conventional method, and if necessary, further converting the product into a pharmaceutically acceptable salt thereof.

10. A process for preparing an optically active 1,5-benzothiazepine compound (3) or a pharmaceutically acceptable salt thereof, which comprises converting an optically active cis-3-hydroxy-1,5-benzothiazepine compound (1) or an acid addition salt obtained by the process of claim 2 into an optically active 1,5-benzothiazepine compound of the formula (3):

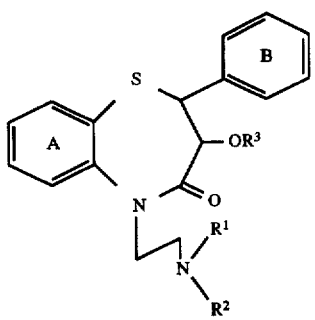

wherein $R^3$ is a lower alkanoyl group and the other symbols are the same as defined above, by a conventional method, and if necessary, further converting the product into a pharmaceutically acceptable salt thereof.

11. A process for preparing an optically active 1,5-benzothiazepine compound (3) or a pharmaceutically acceptable salt thereof, which comprises converting an optically active cis-3-hydroxy-1,5-benzothiazepine compound (1) or an acid addition salt obtained by the process of claim 3 into an optically active 1,5-benzothiazepine compound of the formula (3):

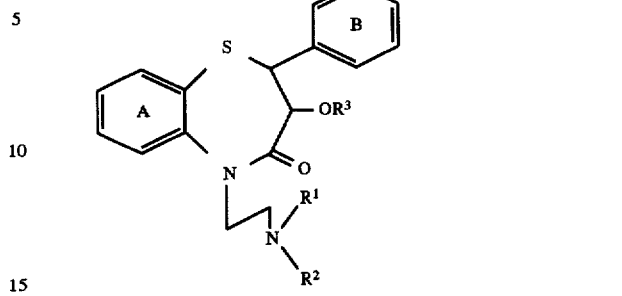

wherein $R^3$ is a lower alkanoyl group and the other symbols are the same as defined above, by a conventional method, and if necessary, further converting the product into a pharmaceutically acceptable salt thereof.

* * * * *